United States Patent
Hueffer et al.

(10) Patent No.: US 7,354,457 B2
(45) Date of Patent: Apr. 8, 2008

(54) TANNING AGENT AND CURING AGENT BASED ON DIALDEHYDES

(75) Inventors: Stephan Hueffer, Ludwigshafen (DE); Gunther Pabst, Mannheim (DE); Tilman Luedecke Taeger, Seeheim-Jugenheim (DE); Stefan Schroeder, Neuleiningen (DE); Gerhard Wolf, Ketsch (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/511,279

(22) PCT Filed: May 2, 2003

(86) PCT No.: PCT/EP03/04603

§ 371 (c)(1), (2), (4) Date: Oct. 22, 2004

(87) PCT Pub. No.: WO03/095681

PCT Pub. Date: Nov. 20, 2003

(65) Prior Publication Data

US 2005/0125906 A1 Jun. 16, 2005

(30) Foreign Application Priority Data

May 7, 2002 (DE) ............... 102 20 493
Jul. 10, 2002 (DE) ............... 102 31 293

(51) Int. Cl.
*C14C 3/08* (2006.01)

(52) U.S. Cl. ............... 8/94.19 R; 252/8.57

(58) Field of Classification Search ........... 8/94.19 R; 252/8.57
See application file for complete search history.

(56) References Cited

U.S. PATENT DOCUMENTS

| | | | | | |
|---|---|---|---|---|---|
| 2,388,086 A | * | 10/1945 | Rust | ............ | 528/227 |
| 2,690,434 A | * | 9/1954 | Sellet et al. | ............ | 528/245.5 |
| 2,868,773 A | * | 1/1959 | Kress | ............ | 530/354 |
| 2,941,859 A | * | 6/1960 | Fein et al. | ............ | 8/94.33 |
| 3,183,054 A | * | 5/1965 | Fischer et al. | ............ | 8/94.33 |
| 3,444,625 A | * | 5/1969 | Giella et al. | ............ | 8/94.1 D |
| 5,534,165 A | * | 7/1996 | Pilosof et al. | ............ | 252/8.91 |
| 2005/0125906 A1 | | 6/2005 | Huffer et al. | | |

FOREIGN PATENT DOCUMENTS

| | | |
|---|---|---|
| DE | 20 03 600 | 8/1971 |
| DE | 22 15 948 | 10/1973 |
| DE | 3811267 | 5/1989 |
| DE | 44 40 846 | 5/1996 |
| DE | 44 44 709 | 6/1996 |

OTHER PUBLICATIONS

Ullmann's Encyclopedia of Industrial Chemistry, Verlag Chemie Weinheim, vol. A15, 5th edition pp. 259-282 1990.
Hans Herfeld, "Bibliothek des leders", Umschau Verlag Frankfurt/Main, vol. 3, p. 191 1984.
Vauck/Müller, "Grundoperationen chemischer verfahrenstechnik", VCH Weinheim, vol. 7, pp. 638-740 and 765-766 1988.
U.S. Appl. No. 10/529,744, filed Mar. 29, 2005, Taeger, et al.
U.S. Appl. No. 10/511,279, filed Oct. 22, 2004, Hueffer, et al.
U.S. Appl. No. 10/543,495, filed Jul. 27, 2005, Hueffer, et al.

* cited by examiner

*Primary Examiner*—Lornam M. Douyon
*Assistant Examiner*—Amina Khan
(74) *Attorney, Agent, or Firm*—Oblon, Spivak, McClelland, Maier & Neustadt, P.C.

(57) ABSTRACT

Tanning agents can be prepared by reacting at least one aldehyde of formula I, with at least one further identical or different aldehyde of formula I,

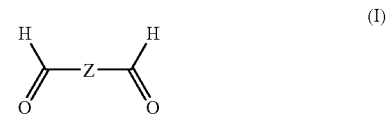

where Z is a single chemical bond, unsubstituted or substituted $C_1$-$C_{12}$-alkylene, unsubstituted or substituted $C_5$-$C_{12}$-cycloalkylene or unsubstituted or substituted $C_6$-$C_{14}$-arylene, the reaction being carried out in the presence of an acidic catalyst and in the presence of at least one further carbonyl compound of formula II

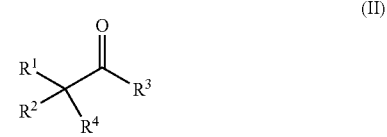

where $R^1$ to $R^4$, independently of one another, are hydrogen, unsubstituted or substituted $C_1$-$C_{12}$-alkyl, unsubstituted or substituted $C_3$-$C_{12}$-cycloalkyl, unsubstituted or substituted $C_7$-$C_{13}$-aralkyl or unsubstituted or substituted $C_6$-$C_{14}$-aryl, with the proviso that, where Z is a single chemical bond or a radical without α-hydrogen atoms, at least one further aldehyde of the formula I, in which Z contains α-hydrogen atoms, or at least one further carbonyl compound of formula II is present.

14 Claims, No Drawings

TANNING AGENT AND CURING AGENT BASED ON DIALDEHYDES

The present invention relates to tanning agents which can be prepared by reacting at least one aldehyde of the formula I,

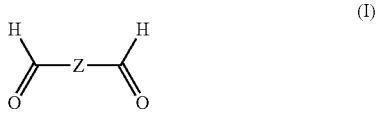

with at least one further identical or different aldehyde of the formula I, where the variables are defined as follows:

Z is a single chemical bond, unsubstituted or substituted $C_1$-$C_{12}$-alkylene, unsubstituted or substituted $C_5$-$C_{12}$-cycloalkylene or unsubstituted or substituted $C_6$-$C_{14}$-arylene, the reaction being carried out in the presence of an acidic catalyst and optionally in the presence of at least one further carbonyl compound of the formula II

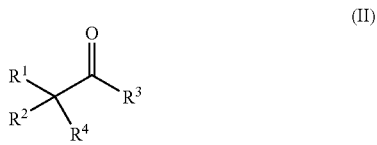

where $R^1$ to $R^4$, independently of one another, are hydrogen, unsubstituted or substituted $C_1$-$C_{12}$-alkyl, unsubstituted or substituted $C_3$-$C_{12}$-cycloalkyl, unsubstituted or substituted $C_7$-$C_{13}$-aralkyl or unsubstituted or substituted $C_6$-$C_{14}$-aryl, with the proviso that, where Z is a single chemical bond or a radical without α-hydrogen atoms, at least one further aldehyde of the formula I, in which Z contains α-hydrogen atoms, or at least one further carbonyl compound of the formula II is present.

The invention furthermore relates to a process for the preparation of these tanning agents, their use as preservatives, in particular their use for pretanning, tanning or retanning of animal hides, and a process for pretanning, tanning and retanning of animal hides by means of the novel tanning agents.

The present invention furthermore relates to a pulverulent active ingredient which contains one or more of the novel tanning agents, a process for the preparation of this pulverulent active ingredient and its use as preservative, and leather which has been produced using the novel tanning agents or by the novel process.

Chrome tanning has been an important chemical treatment in leather production for more than 100 years, cf. for example *Ullmann's Encyclopedia of Industrial Chemistry*, Volume A15, pages 259 to 282 and in particular page 268 et seq., 5th edition (1990), Verlag Chemie Weinheim). For ecological reasons, however, alternatives are being sought for chrome tanning. In conventional chrome tanning, chromium salts are provided in an amount of from 1.5 to 8% by weight, based on the pelt weight of the leather, or even more. A considerable part of this is not bound and enters the wastewater. Although it is possible to free the wastewater from considerable amounts of chromium by chemical treatment with, for example, lime and iron salts, chromium-containing sludges are obtained and have to be disposed of on special landfills or worked up in an expensive procedure.

In addition, chromium-containing leather wastes which can account for from about 8 to 15% by weight, based on the hide weight, and likewise have to be disposed of in an expensive procedure are obtained, for example, in the splitting of the hides and in the leveling of the leathers.

There has been no lack of attempt to reduce the chromium pollution of the wastewaters by, for example, recycling of the chrome tanning liquors or chromium recycling processes. However, these processes were as a whole unsatisfactory and in particular were incapable of solving the problem of the chromium-containing leather wastes.

Furthermore, processes in which some or all of the chromium was replaced by organic tanning agents are known. The use of the syntans, i.e. sulfonated condensates of formaldehyde and phenol or sulfonated naphthalene/formaldehyde condensates, may be mentioned. The use of vegetable tanning agents may furthermore be mentioned. However, both classes of tanning agents result in a higher COD of the wastewaters and are also unsafe for environmental reasons. Moreover, it has been found that the lightfastness of the leathers is often unsatisfactory when sulfonated phenol/formaldehyde condensates are used (*Ullmann's Encyclopedia of Industrial Chemistry*, Volume A15, pages 259 to 282 and in particular page 270 et seq., 5th edition (1990), Verlag Chemie Weinheim).

The use of polymer tanning agents is furthermore known, for example from EP-A 0 792 377. However, the performance characteristics of the leathers obtained by the disclosed process can be further improved.

Furthermore, tanning with the use of aldehydes, in particular dialdehydes, for example glutaraldehyde, is known, cf., for example, H. Herfeld, Bibliothek des Leders, Volume III, page 191, Umschau Verlag Frankfurt/Main, 1984. However, disadvantages are that the shrinkage temperatures do not exceed 70° C. in the case of small amounts of glutaraldehyde (for example, from 0.5 to 0.9% by weight, based on the pelt weight), and that the semifinished products produced therefore cannot be adequately hydroextracted. During shaving, glueing occurs on the flesh side of the leather and adversely affects the quality of the leather. On the other hand, however, for reasons relating to work hygiene, attempts will be made to avoid the use of large amounts of glutaraldehyde.

It is also known that glutaraldehyde in partially or completely acetalated form can be used for tanning, for example as methylacetal (*Ullmann's Encyclopedia of Industrial Chemistry*, Volume A15, pages 259 to 282 and in particular page 273 et seq., 5th edition (1990), Verlag Chemie Weinheim). However, the tanned semifinished product described generally tends to yellow rapidly.

DE-C 38 11 267 discloses that acetalation of glutaraldehyde or other dialdehydes of 2 to 8 carbon atoms with short-chain alkylglycols, alkylpolyglycols, aliphatic alcohols, glycerol or saccharides has advantageous effects. However, the vapor pressure of the dialdehydes, which readily form again from the very hydrolysis-sensitive acetals, is still marked. Moreover, the performance characteristics of the leathers thus obtained can be further improved.

It is an object of the present invention to provide novel tanning agents for the pretanning, tanning and retanning of animal hides, which tanning agents avoid the above-mentioned disadvantages. In particular, it is an object of the present invention to provide a tanning agent which avoids the disadvantages described above.

We have found that this object is achieved by the tanning agents defined at the outset.

In formula I

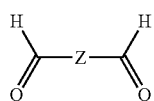

the variables are defined as follows:

Z is a single chemical bond, unsubstituted or substituted $C_1$-$C_{12}$-alkylene, for example —$CH_2$—, —$CH_2$—$CH_2$—, —$(CH_2)_3$—, —$(CH_2)_4$—, —$(CH_2)_5$—, —$(CH_2)_6$—, —$(CH_2)_7$—, —$(CH_2)_8$—, —$(CH_2)_9$—, —$(CH_2)_{10}$—, —$(CH_2)_{11}$—, —$(CH_2)_{12}$—, cis- or trans-CH=CH—, Z- or E-$CH_2$—CH=CH—; preferably —$CH_2$—, —$CH_2$—$CH_2$—, —$(CH_2)_3$—, —$(CH_2)_4$—, —$CH(CH_3)$—, —CH ($C_6H_5$)—, —$CH(CH_3)$—$CH_2$—, syn-$CH(CH_3)$—CH ($CH_3$)—, anti-$CH(CH_3)$—$CH(CH_3)$—, syn-CH ($CH_3$)—$CH(C_6H_5)$—, anti-$CH(CH_3)$—$CH(C_6H_6)$—, —$\{CH(CH_3)\}_3$—, unsubstituted or substituted $C_5$-$C_{12}$-cycloalkylene, for example trans- or cis-1,2-cyclopentanylene, trans- or cis-1,3-cyclopentanylene, trans- or cis-1,3-cyclopent-4-enylene, trans- or cis-1,4-cyclohexanylene, trans- or cis-1,4-cyclohex-2-enylene, trans- or cis-1,3-cyclohexanylene, trans- or cis-1,2-cyclohexanylene, unsubstituted or substituted by one or more $C_1$-$C_4$-alkyl groups, for example methyl, ethyl, n-propyl, isopropyl, n-butyl, sec-butyl, isobutyl or tert-butyl, or one or more halogen atoms, for example fluorine, chlorine, bromine or iodine, or unsubstituted or substituted $C_6$-$C_{14}$-arylene, for example para-phenylene, meta-phenylene, ortho-phenylene, 1,2-naphthylene, 1,3-naphthylene, 1,4-naphthylene, 1,5-naphthylene, 1,6-naphthylene, 1,7-naphthylene, 1,8-naphthylene, 2,3-naphthylene, 2,7-naphthylene, 2,6-naphthylene, 1,4-anthrylene, 9,10-anthrylene, p,p'-biphenylene, unsubstituted or substituted by one or more $C_1$-$C_4$-alkyl groups, for example methyl, ethyl, n-propyl, isopropyl, n-butyl, sec-butyl, isobutyl or tert-butyl, or one or more halogen atoms, for example fluorine, chlorine, bromine or iodine.

In formula II

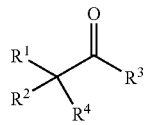

$R^1$ to $R^4$, independently of one another, are hydrogen, unsubstituted or substituted $C_1$-$C_{12}$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl, n-octyl, n-nonyl, n-decyl and n-dodecyl; preferably $C_1$-$C_6$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl and sec-hexyl, particularly preferably $C_1$-$C_4$-alkyl, such as methyl, ethyl, n-propyl, isopropyl, n-butyl, isobutyl, sec-butyl and tert-butyl, very particularly preferably methyl;

unsubstituted or substituted $C_3$-$C_{12}$-cycloalkyl, such as cyclopropyl, cyclobutyl, cyclopentyl, cyclohexyl, cycloheptyl, cyclooctyl, cyclononyl, cyclodecyl, cycloundecyl and cyclododecyl; preferably cyclopentyl, cyclohexyl, cycloheptyl, 2-methylcyclopentyl, 3-methylcyclopentyl, cis-2,4-dimethylcyclopentyl, trans-2,4-dimethylcyclopentyl, 2,2,4,4-tetramethylcyclopentyl, 2-methylcyclohexyl, 3-methylcyclohexyl, 4-methylcyclohexyl, cis-2,5-dimethylcyclohexyl, trans-2,5-dimethylcyclohexyl, 2,2,5,5-tetramethylcyclohexyl, 2-methoxycyclopentyl, 2-methoxycyclohexyl, 3-methoxycyclopentyl, 3-methoxycyclohexyl, 2-chlorocyclopentyl, 3-chlorocyclopentyl, 2,4-dichlorocyclopentyl, 2,2,4,4-tetrachlorocyclopentyl, 2-chlorocyclohexyl, 3-chlorocyclohexyl, 4-chlorocyclohexyl, 2,5-dichlorocyclohexyl, 2,2,5,5-tetrachlorocyclohexyl, 2-thiomethylcyclopentyl, 2-thiomethylcyclohexyl, 3-thiomethylcyclopentyl, 3-thiomethylcyclohexyl and further derivatives;

unsubstituted or substituted $C_7$-$C_{13}$-aralkyl, preferably $C_7$- to $C_{12}$-phenylalkyl, such as benzyl, 1-phenethyl, 2-phenethyl, 1-phenylpropyl, 2-phenylpropyl, 3-phenylpropyl, neophyl (1-methyl-1-phenylethyl), 1-phenylbutyl, 2-phenylbutyl, 3-phenylbutyl and 4-phenylbutyl, particularly preferably benzyl, or unsubstituted or substituted $C_6$-$C_{14}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl, possible substituents of $C_6$-$C_{14}$-aryl groups being:

$C_1$-$C_{12}$-alkyl groups, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl, n-octyl, n-nonyl, n-decyl and n-dodecyl; preferably $C_1$-$C_6$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl and sec-hexyl, particularly preferably $C_1$-$C_4$-alkyl, such as methyl, ethyl, n-propyl, isopropyl, n-butyl, isobutyl, sec-butyl and tert-butyl;

halogens, such as fluorine, chlorine, bromine and iodine, chlorine and bromine being preferred, and/or $C_1$-$C_{12}$-alkoxy groups, preferably $C_1$-$C_6$-alkoxy groups, such as methoxy, ethoxy, n-propoxy, isopropoxy, n-butoxy, isobutoxy, sec-butoxy, tert-butoxy, n-pentyloxy, isopentyloxy, n-hexyloxy and isohexyloxy, particularly preferably methoxy, ethoxy, n-propoxy and n-butoxy.

In a particular embodiment, $R^1$ and $R^2$ in formula II are covalently bonded to one another with formation of a 4- to 13-membered ring. Thus, $R^1$ and $R^2$ together may be, for example, —$(CH_2)_4$—, —$(CH_2)_5$—, —$(CH_2)_6$—, —$(CH_2)_7$—, —$CH(CH_3)$—$CH_2$—$CH_2$—$CH(CH_3)$— or —$CH(CH_3)$—$CH_2$—$CH_2$—$CH_2$—$CH(CH_3)$—.

$R^1$ and $R^2$ are each preferably hydrogen.

Z is very particularly preferably —$(CH_2)_3$—.

The novel reaction is preferably carried out by heating to temperatures of 30 to 130° C., in particular from 20 to 100° C., very particularly from 50 to 80° C. The reaction can be carried out at any desired pressures from 0.1 to 100 bar, atmospheric pressure being preferred. The reaction can be effected in the presence of a solvent, for example of hydrocarbons, preferably toluene, petroleum ether or n-heptane. Halogenated hydrocarbons, for example chloroform, are also suitable in principle. The reaction in aqueous solution or aqueous dispersion is preferred.

It is possible to add dehydrating agents for accelerating the reaction, but the addition of said agents is not necessary. If the reaction is carried out in water as a solvent, the addition of dehydrating agent is of course not reasonable.

According to the invention, the catalysts used are acidic catalysts, for example phosphoric acid, formic acid, acetic acid, acidic silica gels or dilute or concentrated sulfuric acid. If nonaqueous solvents are employed, the use of $P_2O_5$ or molecular sieve is also possible. Usually, from 0.1 to 20, preferably from 1 to 10, mol %, based on I, of catalyst are used.

From 10 minutes to 24 hours, preferably from one to three hours, are reasonable as a reaction time for the novel reaction.

After heating, working-up is usually carried out by first neutralizing the acid, for example aqueous alkali metal hydroxide solution or with aqueous alkali metal hydroxide solution or with aqueous alkali metal carbonate solution or with solid basic alkali metal compounds, for example alkali metal hydroxide, alkali metal carbonate or alkali metal bicarbonate.

The volatile components of the reaction mixture can then be distilled off. As a rule, heating to from 40 to 80° C. under reduced pressure, for example from 10 to 100 mbar, is expedient for this purpose.

In a preferred embodiment, aldehydes of the formula I are reacted with from 1 to 1 000, preferably from 10 to 500, particularly preferably from 20 to 200, mol % of at least one further carbonyl compound of the formula II.

The carbonyl compounds of the formula II used as further reactants preferably carry α-hydrogen atoms.

Particularly preferred are carbonyl compounds of the formula IIa

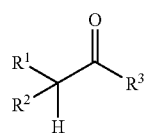

where $R^1$ to $R^3$ are as defined above by way of example in formula II.

In this case too, in a particular embodiment, $R^1$ and $R^2$ are covalently bonded to one another with formation of a 4- to 13-membered ring. Thus, accordingly, $R^1$ and $R^2$ together may be, for example, —$(CH_2)_4$—, —$(CH_2)_5$—, —$(CH_2)_6$—, —$(CH_2)_7$—, —$CH(CH_3)$—$CH_2$—$CH_2$—$CH(CH_3)$— or —$CH(CH_3)$—$CH_2$—$CH_2$—$CH_2$—$CH(CH_3)$—.

$R^1$ and $R^2$ are each particularly preferably hydrogen and $R^3$ is particularly preferably methyl.

Where, in formula I, Z is a single chemical bond or a radical without α-hydrogen atoms, the presence of at least one further aldehyde of the formula I, in which Z contains α-hydrogen atoms, or at least one further carbonyl compound of the formula II is essential.

The excess of the at least one further aldehyde of the formula I or of the at least one further carbonyl compound of the formula II is at least 100 mol %, based on I.

The present invention furthermore relates to a process for the preparation of the novel tanning agents, wherein, taking into account the proviso made above, one or more aldehydes of the formula I are heated in the presence of an acidic catalyst and optionally in the presence of at least one further carbonyl compound of the formula II.

The novel reactions under the conditions described above usually result in the formation of mixtures which are difficult to separate and whose products result from dimerizations, oligomerizations (from 3 to 8 units) and polymerization (9 or more units) of the aldehyde of the formula I, and furthermore from aldol addition reactions, possibly followed, for example, by elimination of water (dehydration), oxidations or intramolecular crosslinking. During the storage of the novel tanning agents, storage-related byproducts may furthermore occur, for example as a result of elimination of water (dehydration), oxidations or dimerization, oligomerization or polymerization and crosslinking.

It is possible to isolate the individual products of the novel reactions and to use them as tanning agents. However, a preferred aspect of the present invention is the use of the reaction products which have been only incompletely further purified or not further purified at all as tanning agents.

The novel tanning agents can be used for the pretanning, tanning and retanning of animal hides. The present invention therefore relates furthermore to the use of the novel tanning agents for the pretanning, tanning and retanning of animal hides and a process for the pretanning, tanning and retanning of animal hides with the use of the novel tanning agents.

The novel process for the pretanning, tanning or retanning of animal hides, also referred to below as novel tanning process, starts from hides of animals such as cattle, pigs, goats or deer, which hides have been pretreated by conventional methods. Whether the animals have been killed, for example by slaughtering, or have died of natural causes is unimportant for the novel tanning process. The conventional pretreatment methods include, for example, liming, deliming, bating and pickling as well as mechanical operations, for example for fleshing the hides.

The novel tanning process is generally carried out by adding one or more novel tanning agents in one portion or in a plurality of portions immediately before or during the tanning step. The novel tanning process is preferably carried out at a pH of from 2.5 to 4, it frequently being observed that the pH increases by from about 0.3 to three units while the novel tanning process is being carried out. The pH can also be increased by from about 0.3 to three units by adding basifying agents.

The novel tanning process is generally carried out at from 10 to 45° C., preferably from 20 to 30° C. A duration of from 10 minutes to 12 hours, preferably from one to three hours, has proven useful. The novel tanning process can be carried out in any desired vessels customary in tanneries, for example by drumming.

In one variant of the novel tanning process, the novel tanning agents are used together with one or more conventional tanning agents, for example with chrome tanning agents, mineral tanning agents, syntans, polymer tanning agents or vegetable tanning agents, as described, for example, in *Ullmann's Encyclopedia of Industrial Chemistry*, Volume A15, pages 259 to 282 and in particular page 268 et seq., 5th edition (1990), Verlag Chemie Weinheim. The weight ratio of novel tanning agent to conventional tanning agent or sum of the conventional tanning agents is expediently from 0.01:1 to 100:1. In an advantageous variant of the novel process, only a few ppm of the conventional tanning agents are added to the novel tanning agents. However, it is particularly advantageous completely to dispense with the admixing of conventional tanning agents.

In a variant of the novel tanning process, one or more novel tanning agents are added in one portion or in a plurality of portions before or during the pretanning, and, in a particular variant, as early as during the pickling.

In a further variant of the novel tanning process, one or more novel tanning agents are added in one portion or in a plurality of portions before or during one or more retanning steps. This variant is referred to below as novel retanning process. The novel retanning process can be carried out under otherwise conventional conditions. Expediently, one or more, i.e. from 2 to 6, treatment steps are chosen and washing with water can be effected between the treatment steps. The temperature during the individual treatment steps is in each case from 5 to 60° C., preferably from 20 to 45° C. Further compositions usually used during retanning are expediently employed, for example fat liquors, polymer tanning agents and acrylate- and/or methacrylate-based fat liquoring agents, retanning agents based on resin and vegetable tanning agents, fillers, leather dyes or emulsifiers.

A further aspect of the present invention relates to leathers produced using the novel tanning agent or by the novel tanning process and/or the retanning process. The novel leathers have an overall advantageous quality, for example smooth grains, more homogeneous tanning over the cross-section, improved tensile strength and body as well as less tendency to discoloration, in particular to yellowing.

In a specific embodiment of the novel tanning process, the novel tanning agents are used in the form of pulverulent active ingredients. The present invention therefore furthermore relates to pulverulent active ingredients containing 10 to 100, preferably from 40 to 90, % by weight of one or more novel tanning agents and from 0 to 90, preferably from 10 to 60, % by weight of one or more additives.

The additives are, as a rule, solid particulate substances. They are preferably selected from starch, silica, for example in the form of silica gel, in particular spheroidal silica gels, sheet silicates, alumina and mixed oxides of silica and aluminum.

Further additives are one or more conventional tanning agents or retanning agents, in particular resin tanning agents, for example the resin tanning agent sold under the name Relugan® D, Tamol® M and Basyntan® DLX from BASF Aktiengesellschaft. Ligninsulfonates are also suitable additives.

The novel pulverulent active ingredients are furthermore characterized by the fact that they consist of fine particles having a mean particle size of from 100 nm to 0.1 mm. The particle diameters conform to a particle diameter distribution which may be narrow or broad. Bimodal particle size distributions are also possible. The particles themselves may be irregular or spherical, spherical particle shapes being preferred. In the novel tanning process or retanning process, the novel pulverulent active ingredients can be metered under particularly hygienic conditions.

The present invention furthermore relates to a process for the preparation of the novel pulverulent active ingredients. The novel process starts from novel tanning agents present in solution, in suspension or emulsion or in isolated form. It is particularly preferable to start from reaction solutions as obtained in the novel preparation process for the preparation of the novel tanning agents.

It has proven useful first to concentrate the reaction solutions to a residual solvent content of 50% by weight or less.

According to the invention, the resulting liquid, solid or oily concentrated reaction solutions are atomized in a spray-dryer, preferably in a spray tower. Spray-dryers are known to the person skilled in the art and are described, for example, in Vauck/Müller, *Grundoperationen chemischer Verfahrenstechnik*, VCH Weinheim, 1988, 7th edition, pages 638-740 and pages 765-766, and in the literature cited therein.

A further aspect of the present invention relates to the use of the novel tanning agents as preservatives, and preservatives containing the novel tanning agents and conventional additives.

The novel tanning agents or preservatives are suitable for preserving surfaces and products, for example cosmetic products.

The examples which follow illustrate the invention in more detail without implying any restriction to the scope of protection.

1. Preparation of the Novel Tanning Agents 1.1 Preparation from Glutaraldehyde and Acetone A 2 liter three-necked flask having a condenser, stirrer and thermometer was loaded with 900 g of a 50% strength by weight aqueous solution of glutaraldehyde (4.5 mol), 420 g (7.2 mol) of acetone and 18 ml of a 50% strength by weight sulfuric acid. Stirring was carried out for 3 hours at 70-73° C., followed by cooling. The condenser was then replaced by a distillation bridge. Acetone was distilled off at a bottom temperature of 78° C. in the course of 60 minutes. The mixture was brought to a pH of 4.5-5.5 with 14 ml of 50% strength by weight aqueous sodium hydroxide solution. Volatile components were then distilled off for a further 20 minutes at 60-65° C. under reduced pressure (10 mbar). 830 g of an amber-colored liquid were obtained. The viscosity was determined as 45 mPaVs (20° C.). GPC analysis showed a broad molar mass distribution (Q=9.6) with $M_n$=450 g.

1.2 Preparation from Glutaraldehyde and Butanone

A 2 liter three-necked flask having a condenser, stirrer and thermometer was loaded with 900 g of a 50% strength by weight aqueous solution of glutaraldehyde (4.5 mol), 520 g (7.2 mol) of butanone and 20 ml of a 50% strength by weight sulfuric acid. Stirring was carried out for 3 hours at 80° C., followed by cooling. 16 ml of a 50% strength by weight aqueous sodium hydroxide solution were added while stirring at 50° C. The condenser was then replaced by a distillation bridge. Thereafter, the mixture was heated for one hour at 10 mbar and from 60 to 65° C. and volatile components were distilled off. 860 g of a brown liquid were obtained. The viscosity was determined as 35 mPaVs (20° C.). GPC analysis showed a broad molar mass distribution (Q=11.3) with $M_n$=420 g.

1.3 Preparation from Glutaraldehyde

A 2 liter three-necked flask having a condenser, stirrer and thermometer was loaded with 1 200 g of a 50% strength by weight aqueous solution of glutaraldehyde (6 mol), and 25 ml of a 50% strength sulfuric acid. Stirring was carried out for 3 hours at 80° C., followed by cooling. 18 ml of a 50% strength by weight aqueous sodium hydroxide solution were added while stirring at 50° C. The condenser was then replaced by a distillation bridge. Thereafter, the mixture was heated for one hour at 10 mbar and from 60 to 65° C. and volatile components were distilled off. 1 020 g of a brown liquid were obtained. The viscosity was determined as 85 mPaVs (20° C.). The GPC analysis showed a broad molar mass distribution (Q=12.8) with $M_n$=680 g.

1.4 Preparation from Glutaraldehyde and Acetaldehyde

A 2 liter three-necked flask having a condenser, stirrer and thermometer was loaded with 800 g of a 50% strength by weight aqueous solution of glutaraldehyde (4 mol), 520 g of a 35% strength by weight aqueous solution of acetaldehyde (4.1 mol) and 20 ml of a 50% strength sulfuric acid. Stirring was carried out for 3 hours at 80° C., followed by cooling. 16 ml of a 50% strength by weight aqueous sodium hydroxide solution were added while stirring at 50° C. Thereafter, the mixture was heated for one hour at 10 mbar and from 60 to 65° C. and volatile components were distilled off. 840 g of an amber-colored liquid were obtained. The viscosity was determined as 22 mPaVs (20° C.). GPC analysis showed a broad molar mass distribution (Q=7.3) with $M_n$=360 g.

1.5 Preparation from Glutaraldehyde and Benzaldehyde

A 2 liter three-necked flask having a condenser, stirrer and thermometer was loaded with 800 g of a 50% strength by weight aqueous glutaraldehyde solution (4 mol), 350 g of benzaldehyde (3.3 mol) and 18 ml of a 50% strength sulfuric acid. Vigorous stirring was carried out over a period of 3 hours at 80° C., followed by cooling. 14 ml of a 50% strength by weight aqueous sodium hydroxide solution were added while stirring at 50° C. The aqueous phase was separated off in a separating funnel. Thereafter, the mixture was heated for 1 hour at 10 mbar and 60-65° C. and volatile components were distilled off. 640 g of an amber-colored liquid were obtained. The viscosity was 38 mPaVs (20° C.). GPC analysis showed a broad molar mass distribution (Q=9.6) with $M_n$=680 g.

1.6 Preparation of a Novel Pulverulent Active Ingredient 200 ml of a 50% strength by weight aqueous starch solution (Maltodextrin plus from . . . ) were added at 50° C. to 300 g of the tanning agent prepared in example 1.1 and thoroughly mixed. The solution was then converted into a beige powder by means of a Lab S1 type spray-drying tower from APV (yield 280 g). The spray-drying tower was operated with the following settings:
Entry temperature 300° C./exit temperature 90° C.
Throughput: 7.5 kg/h
Electric air heater: 9 kW
Compressed air consumption: 7.2 m³/h
Pressure (compressed air): 4 bar

2. Tanning Experiments 2.1 to 2.5 and Comparative Examples, Chromium-free Tanning 350 ml of water and in each case 3% by weight, based on the pickled pelts, of the products according to examples 1.1 to 1.6 were added at 25° C., in a 10 l drum, to about 500 g of cattle pelts pickled at pH 3.0-3.2. After drumming for 45 minutes, the pH was brought to 4.9-5.1 with 0.5% of magnesium oxide (Neutrigan® MO, BASF Aktiengesellschaft) in the course of 6 hours. The liquor was discharged and the hide was washed with 300 ml of water.
The results are shown in table 1.
For comparison,
3% by weight of glutaraldehyde (50% strength by weight aqueous solution, Relugan® GT50 from BASF Aktiengesellschaft, C 2.7)
4% by weight of glutaraldehyde (24% strength by weight aqueous solution, Relugan® GT 24 from BASF Aktiengesellschaft, C 2.8)
5% by weight of a 25% strength by weight aqueous formaldehyde solution (C 2.9) were added
to pickled cattle pelts and in each case further processing was effected analogously to the above.
The shrinkage temperatures were determined according to the method of DIN 53 336 (1977), the DIN method having been modified as follows:
Point 4.1: The sample pieces had the dimensions 3 cm·1 cm and the thickness was not determined;
Point 4.2: only one specimen was tested per leather sample, instead of 2.
Point 6: Omitted.
Point 7: The drying in the desiccator under reduced pressure was omitted.
Point 8: The shrinkage temperature was read when the pointer moved back.

TABLE 1

Tanning with novel tanning agents and comparative experiments; analysis of the novel leathers

| | | Tanning | | Analysis of the leathers | |
|---|---|---|---|---|---|
| No. | Aldehyde I/ carbonyl compound II | | Dose* [% by wt.] | Shrinkage temperature [° C.] | Yellowing [Rating 1-5] |
| 2.1 | Glutaraldehyde/ acetone | | 3 | 77.5 | 2 |
| 2.2 | Glutaraldehyde/ butanone | | 3 | 75 | 3 |
| 2.3 | Glutaraldehyde | | 3 | 76 | 2.5 |
| 2.4 | Glutaraldehyde/ acetaldehyde | | 3 | 74 | 3.5 |
| 2.5 | Glutaraldehyde/ benzaldehyde | | 3 | 76 | 3.5 |
| 2.6 | Glutaraldehyde/ acetone/starch | | 3 | 75 | 2 |
| C 2.7 | Glutaraldehyde 50% by weight | | 3 | 79 | 4 |
| C 2.8 | Glutaraldehyde 24% by weight | | 4 | 75 | 3.5 |
| C 2.9 | Formalin 25% by weight | | 5 | 73 | 2.5 |

*based on the pickled pelts
The rating was effected as in school; 1: very good, 5: poor.

The concentration of glutaraldehyde in the gas phase above the novel tanning agents 1.1 to 1.6 at 25° C. and 40° C. was also determined by GC/MS. Furthermore, the concentration of glutaraldehyde above the tanning liquors from examples 2.1 to 2.6 and C 2.7 and C 2.8 at 25° C. was determined after metering of the tanning agents, according to the above examples.
The results are summarized in table 2.

TABLE 2

Investigations of the determination of the concentration of free glutaraldehyde in the air

| Tanning agent no. | Concentration of glutaraldehyde at 25° C. [ppm] | Concentration of glutaraldehyde at 40° C. [ppm] | Tanning liquor from example | Concentration of glutaraldehyde at 25° C. [ppm] |
|---|---|---|---|---|
| 1.1 | 5 | 8 | 2.1 | 2 |
| 1.2 | 3 | 7 | 2.2 | 1 |
| 1.3 | 3 | 7 | 2.3 | 1 |
| 1.4 | 5 | 9 | 2.4 | 2 |
| 1.5 | 2 | 5 | 2.5 | 2 |
| 1.6 | 2 | 4 | 2.6 | not detectable |

TABLE 2-continued

Investigations of the determination of the
concentration of free glutaraldehyde in the air

| Tanning agent no. | Concentration of glutaraldehyde at 25° C. [ppm] | Concentration of glutaraldehyde at 40° C. [ppm] | Tanning liquor from example | Concentration of glutaraldehyde at 25° C. [ppm] |
|---|---|---|---|---|
| Glutaraldehyde 50% by weight | 12 | 34 | C 2.7 | 8 |
| Glutaraldehyde 24% by weight | 16 | 56 | C 2.8 | 15 |

The invention claimed is:

1. A process for pretanning, tanning or retanning an animal hide, comprising:

obtaining a tanning agent prepared by reacting at least one aldehyde according to formula (I)

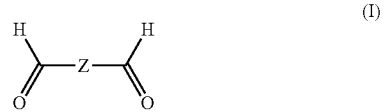

where Z is an unsubstituted or substituted $C_1$-$C_{12}$-alkylene, unsubstituted or substituted $C_5$-$C_{12}$-cycloalkylene or unsubstituted or substituted $C_6$-$C_{14}$-arylene, with at least one further identical or different aldehyde according to formula (I), the reaction being carried out in the presence of an acidic catalyst and at least one further carbonyl compound according to formula (II)

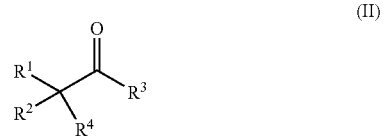

where each of $R^1$ to $R^4$, independently of one another, is hydrogen, unsubstituted $C_1$-$C_{12}$-alkyl, unsubstituted $C_3$-$C_{12}$-cycloalkyl, unsubstituted or substituted $C_7$-$C_{13}$-aralkyl or unsubstituted or substituted $C_6$-$C_{14}$-aryl; and applying the obtained tanning agent to the animal hide.

2. The process according to claim 1, wherein the further carbonyl compound of the formula (II) has α-hydrogen atoms.

3. The process according to claim 1, wherein the further carbonyl compound is a compound according to formula (IIa):

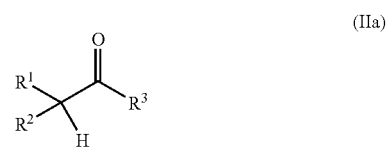

wherein $R^1$ to $R^3$ are as defined in formula (II).

4. The process according to claim 1, wherein $R^3$ in formula (II) is methyl.

5. The process according to claim 1, wherein the tanning agent is in the form of a pulverulent active ingredient.

6. The process according to claim 5, wherein the pulverulent active ingredient comprises from 10 to 100% by weight of the tanning agent in solid form and from 0 to 90% by weight of at least one additive.

7. The process according to claim 6, wherein at least one additive comprises at least one member selected from the group consisting of starch, silica, alumina, mixed oxides of silicon and aluminum.

8. The process according to claim 5, wherein the pulverulent active ingredient is obtained by spray-drying.

9. The process according to claim 1, wherein the tanning agent comprises an oligomer or a polymer including the aldehyde of formula (I) and an identical aldehyde of formula (I).

10. The process according to claim 1, wherein the tanning agent comprises a dimer including the aldehyde of formula (I) and an identical aldehyde of formula (I).

11. The process according to claim 1, where Z is —(CH$_2$)$_3$— in formula (I).

12. The process according to claim 1, where $R^1$ to $R^4$ in formula (II), independently of one another, are hydrogen, $C_1$-$C_{12}$-alkyl, $C_3$-$C_{12}$-cycloalkyl, $C_7$-$C_{13}$-aralkyl or $C_6$-$C_{14}$-aryl.

13. The process according to claim 1, wherein $R^1$ and $R^2$ in formula (II) are each hydrogen.

14. The process according to claim 1, wherein the acid catalyst is selected from the group consisting of phosphoric acid, formic acid, acetic acid, acidic silica gel, dilute sulfuric acid, and concentrated sulfuric acid.

* * * * *